(12) United States Patent
Janzig

(10) Patent No.: US 9,776,010 B2
(45) Date of Patent: *Oct. 3, 2017

(54) MEDICAL LEAD FASTENER INCLUDING INTEGRATED CLAMP

(71) Applicant: Medtronic, Inc., Minneapolis, MN (US)

(72) Inventor: Darren A. Janzig, Center City, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/196,232

(22) Filed: Jun. 29, 2016

(65) Prior Publication Data

US 2016/0375255 A1 Dec. 29, 2016

Related U.S. Application Data

(63) Continuation of application No. 14/063,772, filed on Oct. 25, 2013, now Pat. No. 9,381,367.

(51) Int. Cl.
*A61N 1/00* (2006.01)
*A61N 1/372* (2006.01)
(Continued)

(52) U.S. Cl.
CPC ........... *A61N 1/372* (2013.01); *A61N 1/3752* (2013.01); *H01R 13/5224* (2013.01);
(Continued)

(58) Field of Classification Search
CPC .. A61N 1/372; A61N 1/3752; H01R 13/5224; H01R 13/621; H01R 13/62905; H01R 2201/12; H01R 31/06
See application file for complete search history.

(56) References Cited

U.S. PATENT DOCUMENTS 4,784,141 A 11/1988 Peers-Trevarton
5,951,595 A 9/1999 Moberg et al.
(Continued)

FOREIGN PATENT DOCUMENTS

WO 2009058879 A2 5/2009

OTHER PUBLICATIONS

International Search Report and Written Opinion from International Patent Application No. PCT/US2014/061764, mailed Jan. 5, 2015, 12 pages.

(Continued)

*Primary Examiner* — George Manuel
(74) *Attorney, Agent, or Firm* — Shumaker & Sieffert, P.A.

(57) ABSTRACT

This disclosure includes techniques for securing the proximal ends of a medical lead to the connector block of an IMD with a fastener device that incorporates a flexible clamp. A fastener device for a medical device comprising a flexible clamp forming a clamp aperture, wherein the flexible clamp includes a clamp protrusion configured to facilitate actuation of the flexible clamp, a rigid body, wherein the rigid body connects to and surrounds the flexible clamp, and an actuator configured to actuate on the clamp protrusion to change a perimeter of the clamp aperture, wherein the change of the perimeter of the clamp aperture by the actuator is configured to apply a compressive force about a perimeter of an electrical contact of a medical lead in the clamp aperture to electrically and mechanically connect the medical lead to the fastener device.

20 Claims, 14 Drawing Sheets

(51) Int. Cl.
*A61N 1/375* (2006.01)
*H01R 13/52* (2006.01)
*H01R 13/621* (2006.01)
*H01R 13/629* (2006.01)
*H01R 31/06* (2006.01)

(52) U.S. Cl.
CPC ..... *H01R 13/621* (2013.01); *H01R 13/62905* (2013.01); *H01R 31/06* (2013.01); H01R 2201/12 (2013.01)

(56) References Cited

U.S. PATENT DOCUMENTS

| | | | |
|---|---|---|---|
| 6,390,843 | B1 | 5/2002 | Lim |
| 6,428,368 | B1 * | 8/2002 | Hawkins .............. A61N 1/3752 439/271 |
| 6,741,892 | B1 | 5/2004 | Meadows et al. |
| 7,798,864 | B2 | 9/2010 | Barker et al. |
| 7,899,549 | B2 | 3/2011 | Sweeney et al. |
| 8,075,969 | B2 | 12/2011 | Anderson et al. |
| 9,381,367 | B2 | 7/2016 | Janzig |
| 2009/0233491 | A1 | 9/2009 | Barker et al. |
| 2011/0039445 | A1 | 2/2011 | Boyd et al. |
| 2012/0245657 | A1 | 9/2012 | Lim |

OTHER PUBLICATIONS

International Preliminary Report on Patentability from International Application No. PCT/US2014/061764, mailed May 6, 2016, 8 pages.
Prosecution History from U.S. Pat. No. 9,381,367, dated Nov. 22, 2013 through Jun. 6, 2016, 83 pages.

* cited by examiner

MEDICAL LEAD FASTENER INCLUDING INTEGRATED CLAMP

This application is a continuation of U.S. patent application Ser. No. 14/063,772, filed Oct. 25, 2013 and entitled "MEDICAL LEAD FASTENER INCLUDING INTEGRATED CLAMP," the entire content of which is incorporated herein by reference.

TECHNICAL FIELD

The disclosure is related to techniques for fastening medical leads.

BACKGROUND

Implantable medical devices (IMDs) may be used to treat a variety of medical conditions. Some IMDs may include medical leads for sensing and/or delivery of electrical stimulation therapy to a patient via implanted electrodes. For example, an electrical stimulation device may include an implantable electrical stimulation generator and one or more implantable leads carrying electrodes. In some cases, implantable electrodes may be coupled to an external electrical stimulation generator via one or more percutaneous leads or fully implanted leads.

Example IMDs that may include medical leads include neurostimulators, cardiac monitors, cardiac defibrillators, cardiac pacemakers, and others. Electrical stimulation therapy may include stimulation of nerve, muscle, or brain tissue, or other tissue within a patient. An electrical stimulation device may be fully implanted within the patient. Medical electrical stimulators have been proposed for use to relieve a variety of symptoms or conditions such as heart disease, chronic pain, tremor, Parkinson's disease, depression, epilepsy, migraines, urinary or fecal incontinence, pelvic pain, sexual dysfunction, obesity, and gastro paresis. An electrical stimulator may be configured to deliver electrical stimulation therapy via medical leads that include electrodes implantable proximate to the heart, spinal cord, pelvic nerves, gastrointestinal organs, peripheral nerves, or within the brain of a patient. Stimulation proximate the spinal cord, within the brain, and proximate peripheral nerves are often referred to as spinal cord stimulation (SCS) deep brain stimulation (DBS), and peripheral nerve stimulation (PNS), respectively.

SUMMARY

This disclosure includes techniques for securing the proximal ends of a medical lead to the connector block of an IMD with a fastener device that incorporates a flexible clamp connected to a rigid block. In some examples, the flexible clamp and the rigid block may represent a unitary component. In the same or different examples, the flexible clamp and the rigid block may comprise a conductive material that provide a conductive path from an electrical contact of the medical lead and the electronics of the IMD.

In one example, this disclosure is directed to a fastener device for a medical device comprising a flexible clamp forming a clamp aperture. The flexible clamp includes a clamp protrusion configured to facilitate actuation of the flexible clamp, a rigid body. The rigid body connects to and surrounds the flexible clamp, and an actuator configured to actuate on the clamp protrusion to change a perimeter of the clamp aperture. The change of the perimeter of the clamp aperture by the actuator is configured to apply a compressive force about a perimeter of an electrical contact of a medical lead in the clamp aperture to electrically and mechanically connect the medical lead to the fastener device.

In another example, this disclosure is directed to a method comprising inserting a proximal end of a medical lead including at least one electrode into a clamp aperture defined by a flexible clamp of a fastener device including a flexible clamp block of an implantable medical device. The fastener device includes the flexible clamp forming the clamp aperture. The flexible clamp includes a clamp protrusion configured to facilitate actuation of the flexible clamp, a rigid body. The rigid body connects to and surrounds the flexible clamp, and an actuator configured to actuate on the clamp protrusion to change a perimeter of the clamp aperture. The change in the perimeter of the clamp aperture by the actuator is configured to apply a compressive force about a perimeter of an electrical contact of a medical lead in the clamp aperture to electrically and mechanically connect the medical lead to the fastener device. The method further includes actuating the actuator configured to actuate the clamp protrusion to apply a compressive force about the perimeter of the electrical contact to electrically and mechanically connect the medical lead to the fastener device.

In another example, this disclosure is directed to an implantable medical device implantable medical device comprising a processor, a power supply, a stimulation generator, a housing forming a substantially sealed enclosure, with the processor, the power supply, and the stimulation generator being located within the substantially sealed enclosure, and a connector block configured to provide an electrical connection between the stimulation generator and a medical lead. The connector block includes at least one fastener device comprising a flexible clamp forming a clamp aperture. The flexible clamp includes a clamp protrusion configured to facilitate actuation of the flexible clamp, a rigid body. The rigid body connects to and surrounds the flexible clamp, and an actuator configured to actuate on the clamp protrusion to change a perimeter of the clamp aperture. The change of the perimeter of the clamp aperture by the actuator is configured to apply a compressive force about a perimeter of an electrical contact of a medical lead in the clamp aperture to electrically and mechanically connect the medical lead to the fastener device.

The details of one or more examples of this disclosure are set forth in the accompanying drawings and the description below. Other features, objects, and advantages of this disclosure will be apparent from the description and drawings, and from the claims.

DETAILED DESCRIPTION

This disclosure includes techniques for securing the proximal ends of a medical lead to the connector block of an IMD with a fastener device that incorporates a flexible clamp. In some references, a connector block is instead referred to as a header of the IMD. In particular, structures for retaining a medical lead may include acutatable clamping mechanisms configured to electrically and mechanically connect a medical lead to an IMD. Such a flexible clamping mechanism may form clamp apertures configured to receive the proximal end of a medical lead. Actuating the flexible clamping mechanism may change a perimeter of the clamp aperture to apply a compressive force about a perimeter of an electrical contact of a medical lead in the proximal end of the medical lead, thereby electrically and mechanically connecting the medical lead to the flexible clamping mechanism.

The disclosed fastener devices may further include a rigid body. The rigid body may have features that provide dimensional precision to the location of the proximal end of a medical lead secured by a fastener device. This may improve sealing of the fastener device and lead interface by locating the proximal end of the medical lead precisely within the connector block. The rigid body may further provide for a stable structure for welding conductors, such as feedthrough pins, of feedthroughs that pass through a housing of an IMD in order to provide an electrical connection between a conductor on the proximal end of the lead and the conductors of the feedthroughs.

Other connector blocks may utilize a setscrew in combination with a setscrew block to fixate the medical lead to the IMD. Therefore, during implantation of the IMD, the user turns the setscrew in the setscrew block to pinch the medical lead between the contact surface of the setscrew and the contact surface of the setscrew block. By pinching the medical lead, the user is using the setscrew to apply a non-uniform force(s) and/or pressure(s), e.g., a point load, across the contact surface of the setscrew and the medical lead and across the contact surface of the setscrew block and the medical lead. The disclosed examples may instead prevent crushing of the medical lead connector ring as the load is applied by the flexible clamp in a uniform manner.

Figure 1:
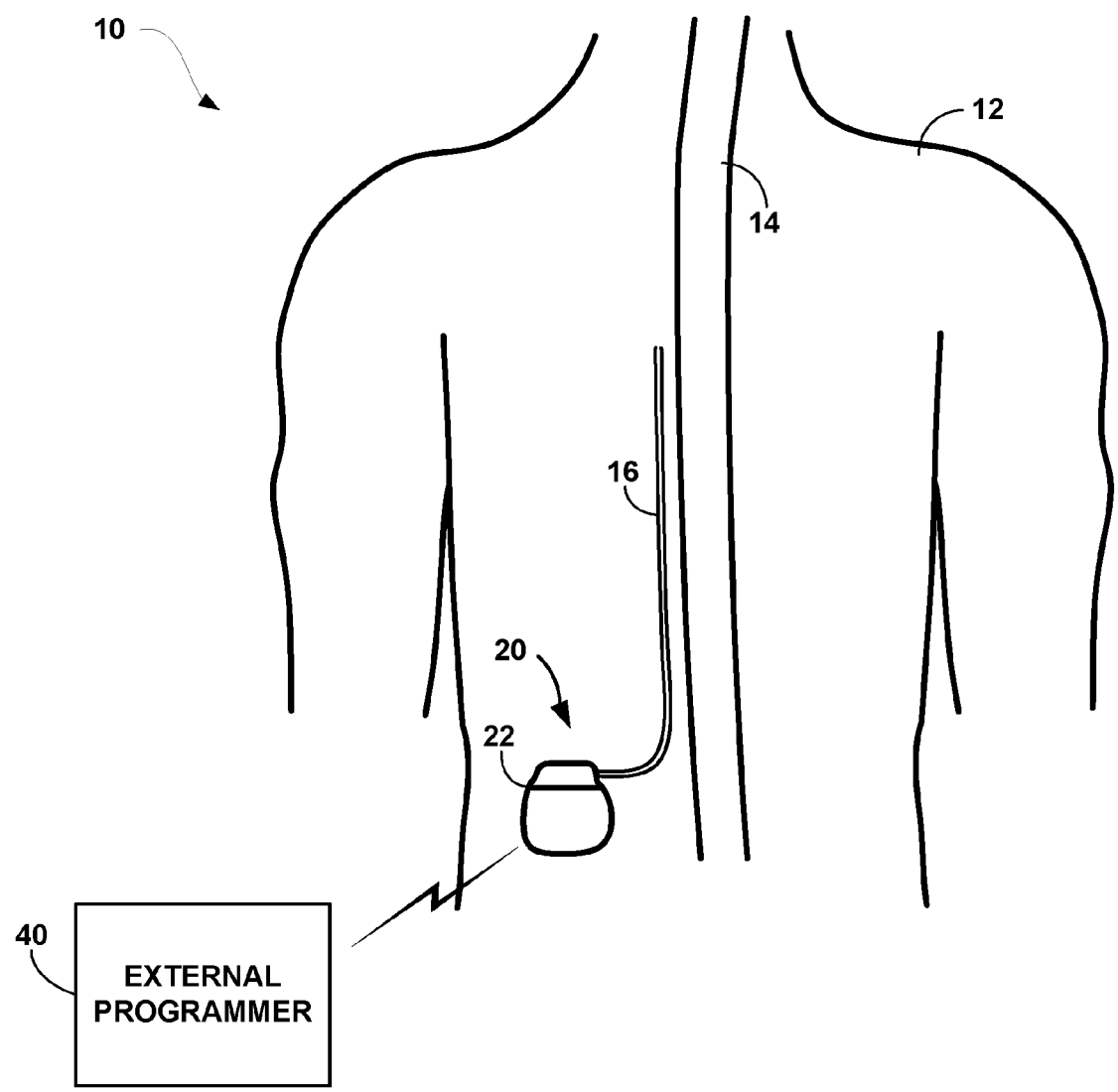
FIG. 1 is a conceptual diagram of a medical system that includes an IMD with medical leads configured to deliver spinal cord stimulation (SCS) therapy.

FIG. 1 illustrates an example medical system 10 that includes an IMD 20 with a medical lead 16 configured to deliver SCS therapy. IMD 20 is configured to deliver therapy to patient 12 through medical lead 16. Medical lead 16 is connected to IMD 20 by connector block 22. In some references, a connector block, such as connector block 22, is instead referred to as a header of the IMD. In any event, connector block 22 provides the means for forming an electrical connection between electrical contacts of medical lead 16 and feedthrough pins of feedthroughs that pass through the housing of IMB 20, which forms a hermetically sealed enclosure for the electronic components of IMB 20.

IMD 20 may include a power sources as well as one or more processors, microprocessors, internal memory, and other electronic circuitry for executing software or firmware to provide the functionality described herein. The software executing thereon may perform a variety of therapy-related operations, one such therapy operation may be stimulation of spinal cord 14 through medical lead 16 operatively (i.e. electrically and/or mechanically connected) connected to IMD 20 by connector block 22.

Connector block 22 is configured to receive the proximal end of medical lead 16. Connector block 22 includes one or more fasteners with actuatable clamps, such as fastener device 24 of FIG. 6 or fastener device 300 of FIG. 11, which are configured to secure the proximal ends of one or more medical leads 16 to IMD 20. Connector block 22 may be comprised of conductive or non-conductive material.

Medical system 10 further includes external programmer 40. In different examples, external programmer 40 may include an external medical device, a programming device, a remote telemetry station, a physician-activated device, a patient-activated device, a display device or any other type of device capable of sending and receiving signals to and from IMD 20. In some implementations, IMD 20 generates content to display on external programmer 40. In other implementations, external programmer 40 communicates instructions to IMD 20 based on the content received from a cloud server, a computer system, and/or a mobile device.

As described herein, IMD 20, and the software executing thereon, provides a platform for providing therapy to spinal cord 14 through medical lead 16. For example, IMD 20 may be configured to receive and process electrical signals produced by the body of patient 12 using medical lead 16. IMD 20 may also use medical lead 16 to deliver therapy, such as SCS therapy, to spinal cord 14 of patient 12. In other examples, one or more medical leads 16 may be dedicated by IMD 20 to receive electrical signals, and one or more medical leads 16 may be dedicated to delivering therapy to spinal cord 14 of patient 12.

In some examples, IMD 20 may implement techniques for automated receiving and processing of electrical signals indicating a need for therapy. For example, IMD 20 may allow a user by communicating with external programmer 40, control over one or more therapy techniques used by IMD 20 in response to IMD 20 receiving and processing electrical signals from medical lead 16 indicating a need for treatment. In another example, a user may use external programmer 40 to provide pre-determined responses for therapy through medical lead 16 to respond to IMD 20 receiving and processing electrical signals from medical lead 16 indicating a need for treatment.

In the example of FIG. 1, IMD 20 is illustrated as an IMD for providing therapy to a spinal cord. However, in other examples, IMD 20 may be a neurostimulator, cardiac monitor, cardiac defibrillator, cardiac pacemakers, or any other type of simulation and/or sensing device that utilizes one or more medical leads.

Figure 2:
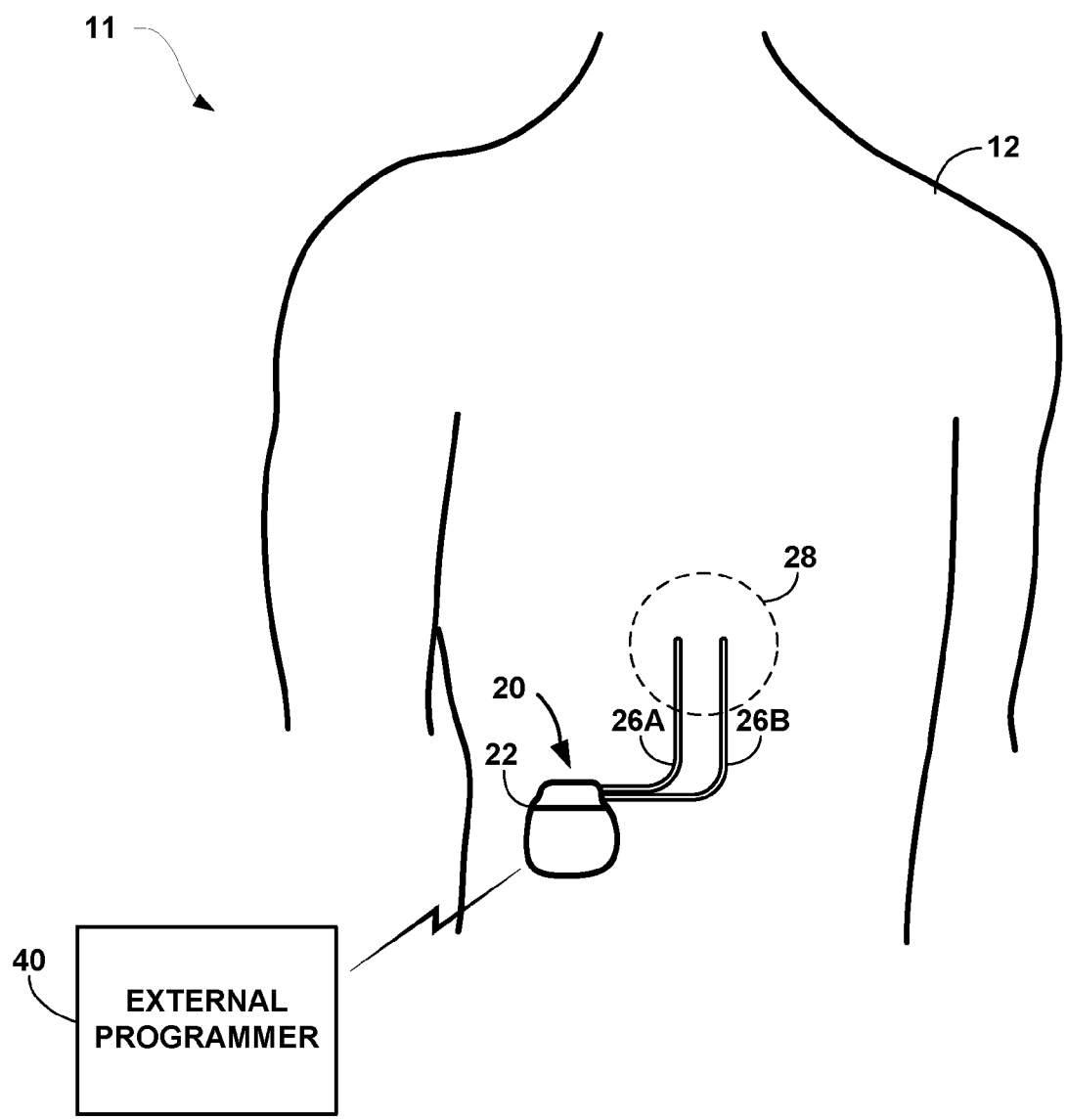
FIG. 2 is a conceptual diagram of a medical system that includes an IMD with medical leads configured to deliver gastric stimulation therapy.

FIG. 2 illustrates an example medical system 11 that includes an IMD 20 with medical leads 26A, 26B configured to deliver gastric stimulation therapy 28. In the example of FIG. 2, medical system 11 includes an IMD 20 to deliver therapy through medical leads 26A, 26B connected operatively to IMD 20 by connector block 22 using a fastener, such as fastener device 24 as described in FIG. 6 or fastener device 300 as described in FIG. 11. As described herein, IMDs deliver therapy through one or more medical leads 26A, 26B based on external programmer 40 and/or internal programming for software that, as described, can efficiently deliver therapy to targeted areas. In this example, connector block 22 may be the result of multiple components.

In the example of FIG. 2, medical system 11 includes components of FIG. 1, such as patient 12, IMD 20, connector block 22, and external programmer 40. In the example of FIG. 2, medical system 11 further includes one or more medical leads 26A, 26B, and stimulation therapy 28.

Medical leads 26A, 26B may include one or more electrodes. In the example illustrated in FIG. 2, medical leads 26A, 26B may each include a respective tip electrode and ring electrode located near a distal end of their respective medical leads 26A, 26B. When implanted, the tip electrodes and/or the ring electrodes are placed relative to or in a selected tissue, muscle, nerve or other location within the patient.

Medical leads 26A, 26B are connected at a proximal end to IMD 20 by connector block 22. Connector block 22 may include one or more fasteners, such as fastener device 24 that interconnects with one or more contact rings located on the proximal end of medical leads 26A, 26B. Medical leads 26A, 26B are operatively connected to one or more of the electrical components within housing 25. One or more conductors (not shown in FIG. 2) extend within medical leads 26A, 26B from the contact rings long the length of the medical lead to engage the ring electrode and the tip electrode respectively. In some examples, medical leads 26A, 26B may each include a plurality of ring electrodes, such as four or eight electrodes. For example, DBS therapy may utilize medical leads including four ring electrodes, whereas SCS therapy may utilize medical leads including eight ring electrodes. In any case, each of the tip electrodes (if present) and the ring electrodes are operatively coupled to a respective conductor within its associated medical lead bodies. For example, a first electrical conductor can extend along the length of the body of medical lead 26A from connector block 22 and operatively couple to the tip electrode and a second electrical conductor can extend along the length of the body of medical lead 26A from connector block 22 and operatively couple to the ring electrode. The respective conductors may be operatively coupled to circuitry, such as a therapy module 34 as described in FIG. 4, of IMD 20 via connections in connector block 22.

In different examples, stimulation 28 may instead include peripheral nerve stimulation (PNS) or peripheral nerve field stimulation (PNFS) therapy, and/or any other stimulation that can be provided by a neurostimulator, a cardiac monitor, a cardiac defibrillator, a cardiac pacemaker, or any other type of mobile or non-mobile computing device suitable for performing the techniques described herein.

IMD 20 may also provide sensing functions in addition to or alternatively to stimulation functions. For example, IMD 20 may be configured to receive and process electrical signals produced by the body of patient 12 using medical leads 26A, 26B to indicate a need for therapy. After a need for therapy is detected by IMD 20, IMD 20 may respond by using medical leads 26A, 26B to deliver therapy, such as stimulation 28, to the body of patient 12. In other examples, one or more medical leads 26A, 26B may be dedicated by IMD 20 to receiving electrical signals and/or delivering therapy, such as stimulation 28 to the body of patient 12.

In some examples, IMD 20 may implement techniques for automated therapy through one or more medical leads 26A, 26B. For example, IMD 20 may allow a user, by communicating with external programmer 40, control over therapy techniques used by IMD 20 in response to detecting and recognizing an irregularity requiring treatment. In another example, a user may use external programmer 40 to provide pre-determined therapy responses, such as stimulation 28, after determining a need for therapy through one or more medical leads 26A, 26B.

In the example of FIG. 2, IMD 20 is illustrated as an IMD for providing therapy to the torso of patient 12. However, in other examples, IMD 20 may be a neurostimulator, cardiac monitor, cardiac defibrillator, cardiac pacemakers, or any other type of mobile or non-mobile computing device suitable for performing the techniques described herein.

Figure 3:
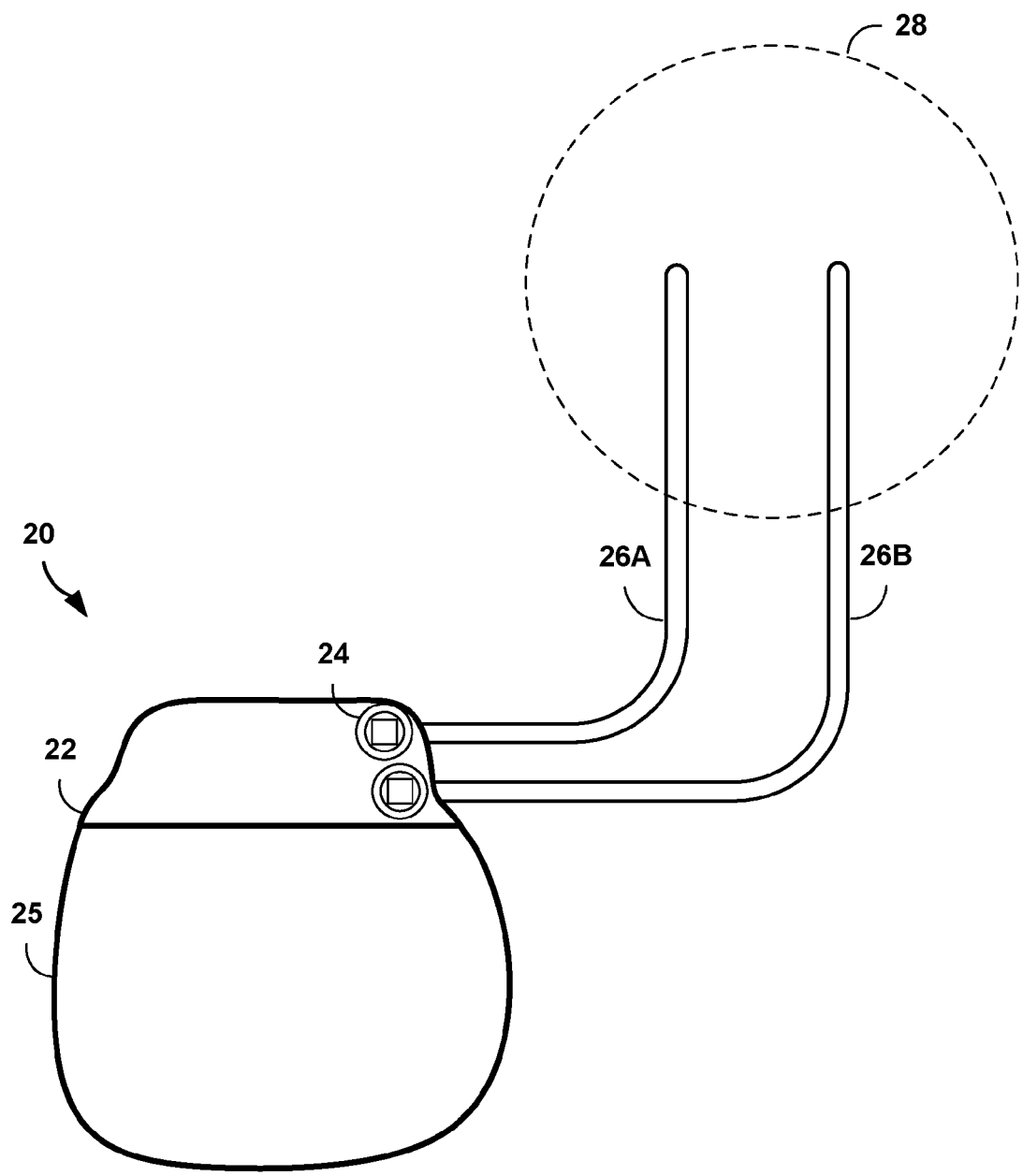
FIG. 3 is a conceptual diagram of an IMD with a fastener device configured to secure a medical lead to the IMD.

FIG. 3 is a conceptual diagram illustrating an example IMD 20 with a fastener device 24 configured to secure medical leads 26A, 26B to the IMD. In the example of FIG. 3, IMD 20 includes several components of medical systems 10, 11 in FIGS. 1-2, such connector block 22, medical leads 26A, 26B, and stimulation 28. In the example of FIG. 3, IMD 20 further includes housing 25 and fastener device 24.

Housing 25 of IMD 20 can be formed from conductive materials, non-conductive materials or a combination thereof. As described herein, housing 25 of IMD 20 may provide a substantially sealed environment for one or more processors, memories, transmitters, receivers, transceivers, sensors, sensing circuitry, therapy circuitry, antennas, power sources, and other components of IMD 20. In the example of FIG. 1-2, IMD 20 delivers therapy, such as stimulation 28 therapy, through one or more medical leads 26A, 26B connected operatively to IMD 20 by connector block 22 utilizing one or more fasteners, such as fastener device 24 as described in FIG. 6.

In the example of FIG. 3, connector block 22 of IMD 20 includes two fastener devices 24 each utilized to secure a respective medical lead 26A, 26B. In another example, connector block 22 of IMD 20 may include one or more than two fastener devices 24 along the border of connector block 22 to allow an operative connection of two or more medical leads to IMD 20.

Figure 4:
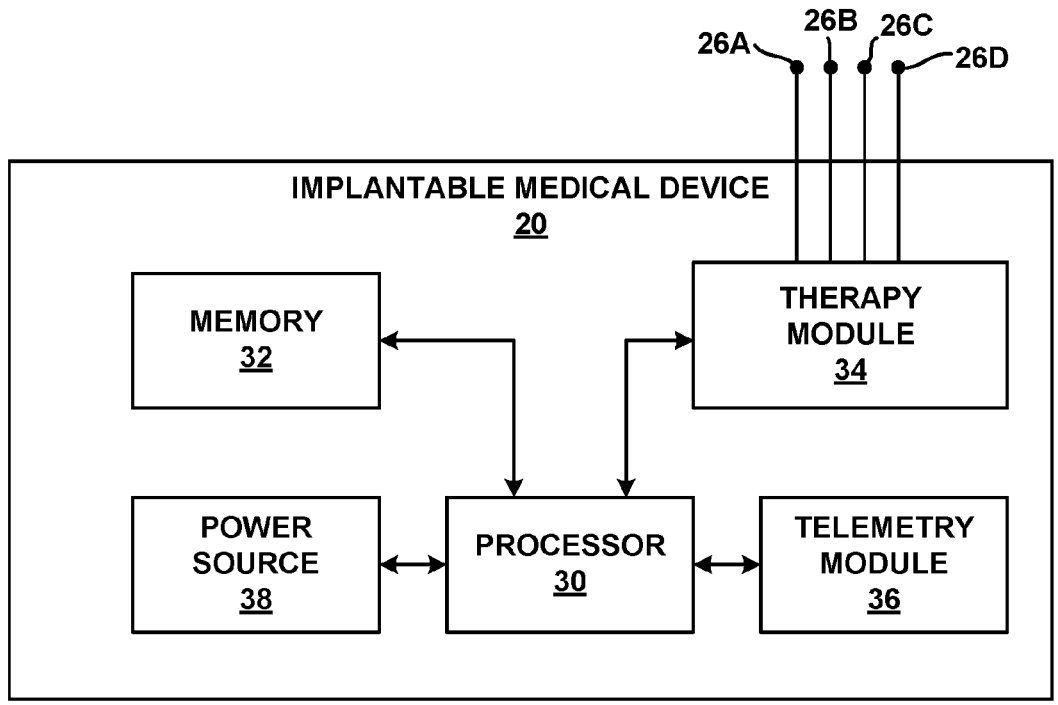
FIG. 4 is a functional block diagram of an IMD configured to deliver stimulation therapy.

FIG. 4 is a functional block diagram illustrating various components of an IMD. As shown in FIG. 4, IMD 20 includes processor 30, memory 32, therapy module 34, telemetry module 36, power source 38, and other various hardware components that provide functionality for operation of the device. For example, IMD 20 includes one or more programmable processors 30 configured to operate according to executable instructions, typically stored in a computer-readable medium or memory 32 such as static, random-access memory (SRAM) device or Flash memory device. IMD 20 may include additional discrete digital logic or analog circuitry not shown in FIG. 4.

Therapy module 34 may connect to one or more medical leads 16, 26A-26D. IMD 20 may utilize therapy module 34 connected to one or more medical leads 16, 26A-26D to detect and recognize irregularities with the patient that require treatment and/or therapy based on instructions from processor 30. In another example, IMD 20 may utilize therapy module 34 connected to one or more medical leads 16, 26A-26D to provide treatment and/or therapy, such as stimulation 28 as described and shown in FIGS. 2-3, based on instructions from processor 30.

Telemetry module 34 may comprise any unit capable of facilitating wireless data transfer between IMD 20 and an external programmer 40, where external programmer 40 may comprise an external medical device, a programming device, a remote telemetry station, a physician-activated device, a patient-activated device, a display device or any other type of device capable of sending and receiving signals to and from IMD 20. Telemetry module 34 and external programmer 40 are respectively coupled to one or more antennas for facilitating the wireless data transfer. Telemetry module 34 may be configured to perform any type of wireless communication. For example, telemetry module 34 may send and receive radio frequency (RF) signals, infrared (IR) frequency signals, or other electromagnetic signals. Any of a variety of modulation techniques may be used to modulate data on a respective electromagnetic carrier wave. Alternatively, telemetry module 34 may use sound waves for communicating data, or may use the patient's tissue as the transmission medium for communicating with a programmer positioned on the skin of a patient. In any event, telemetry module 34 facilitates wireless data transfer between IMD 20 and external programmer 40.

Power source 38 may be a rechargeable battery, such as a lithium ion or nickel metal hydride battery. Other rechargeable or conventional batteries may also be used. In some examples, external programmer 40 may be configured to recharge IMD 20 in addition to programming IMD 20.

Figure 5:
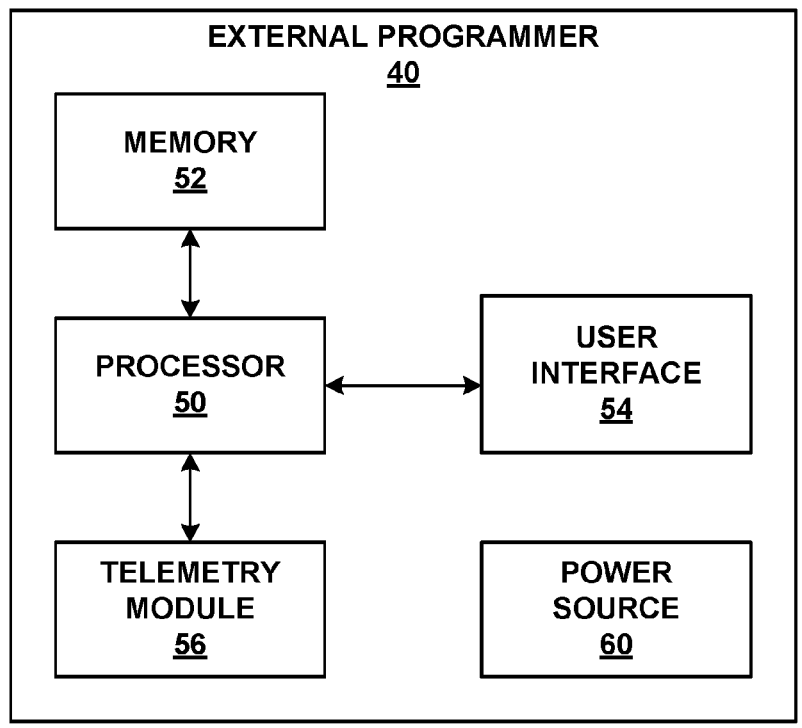
FIG. 5 is a functional block diagram of an IMD configured to deliver stimulation therapy.

FIG. 5 is a functional block diagram illustrating various components of external programmer for an IMD. As shown in FIG. 5, external programmer 40 includes user interface 54, processor 50, memory 52, telemetry module 56, and power source 60. A clinician or patient interacts with user interface 54 in order to manually change the parameters of a therapy program, change therapy programs within a therapy of programs, view therapy information, view historical therapy regimens, establish new therapy regimens, or otherwise communicate with IMD, such as IMD 20 in FIGS. 1-2, or view or edit programming information.

User interface 54 may include a screen and one or more input buttons, that allow external programmer 40 to receive input from a user. Alternatively or additionally, user interface 54 may additionally or only utilize a touch screen display. The screen may be a liquid crystal display (LCD), dot matrix display, organic light-emitting diode (OLED) display, touch screen, or any other device capable of delivering and/or accepting information.

Input buttons for user interface 54 may include a touch pad, increase and decrease buttons, emergency shut off button, and other buttons needed to control the therapy, as described above with regard to patient programmer 40. Processor 50 controls user interface 54, retrieves data from memory 52 and stores data within memory 52. Processor 50 also controls the wireless transmission of data through telemetry module 56 to an IMD, such as IMD 20 in FIGS. 1-2, by transmitting data to telemetry module 36 as described in FIG. 4. The transmitted data may include therapy program information specifying various drug delivery program parameters. Memory 52 may include operational instructions for processor 50 and data related to therapy for the patient.

Power source 60 may be a rechargeable battery, such as a lithium ion or nickel metal hydride battery. Other rechargeable or conventional batteries may also be used. In some cases, external programmer 40 may be used when coupled to an alternating current (AC) outlet, i.e., AC line power, either directly or via an AC/DC adapter. In some examples, external programmer 40 may be configured to recharge IMD 20 in addition to programming IMD 20.

Figure 6:
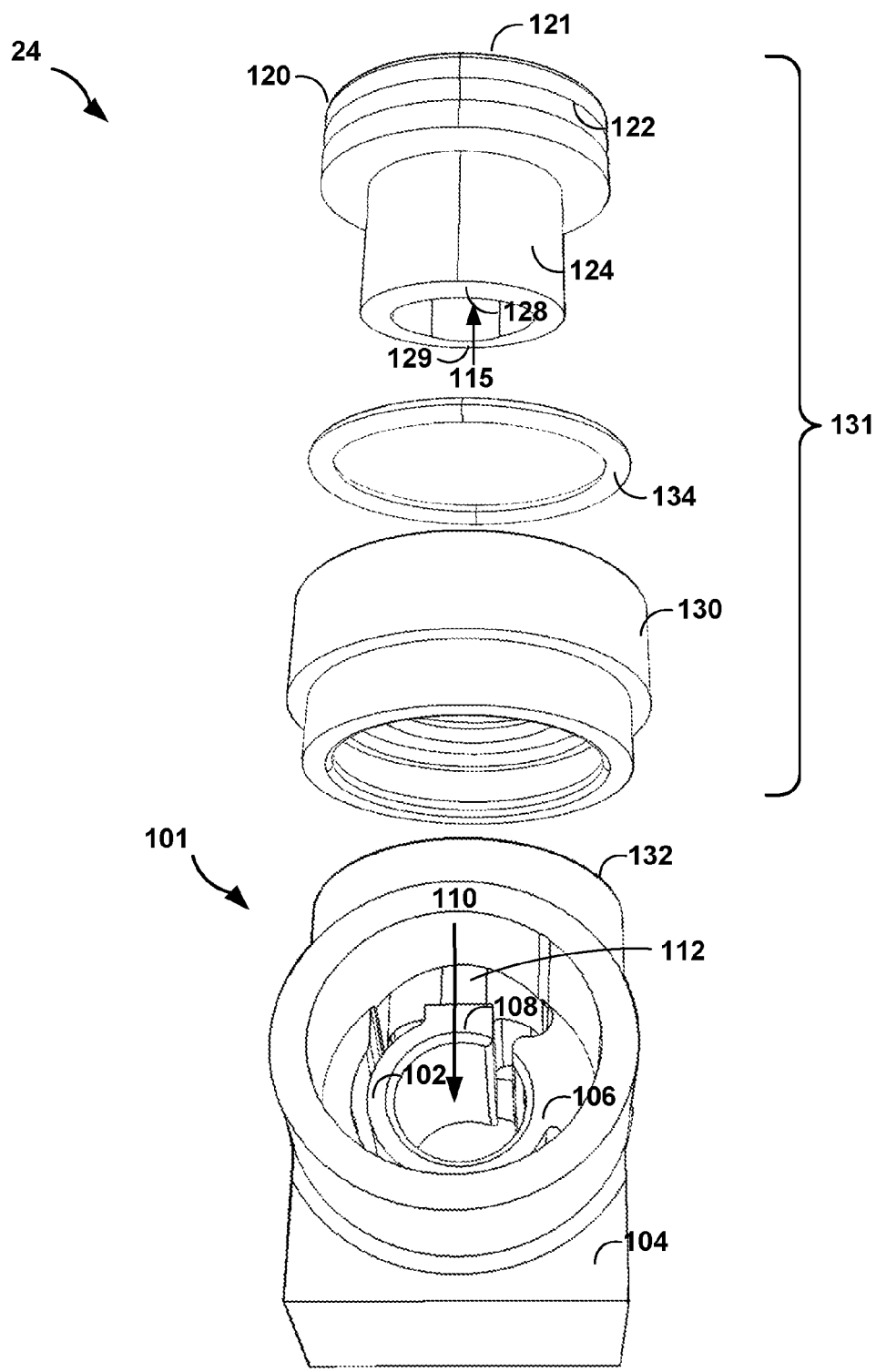
FIG. 6 is a conceptual diagram of a fastener device, including a rotatable actuation member and an outer fixed member configured to actuate on a clamp protrusion.

FIG. 6 illustrates an exploded view of the components of fastener device 24, including actuator 131. Actuator 131 includes outer fixed member 130, O-ring 134 and rotatable actuation member 120. Fastener device 24 further includes clamp block 101, which includes clamp 102 and rigid body 104. Actuator 131 facilitates opening and closing of clamp 102 by the rotation of rotatable actuation member 120. In particular, rotation of rotatable actuation member 120 causes cam member 124 to act on clamp protrusion 112 to open and close clamp 102.

O-ring 134 serves to seal the interior of fastener device 24 from an external environment. In the example of FIG. 6, O-ring 134 is a circular shape and positioned in groove 122 between top portion 121 of rotatable actuation member 120 and outer fixed member 130 as described herein. O-ring 134 may be an elastic material, such as rubber, plastic, or any other elastic material that provides a fluidic isolation seal to prevent unwanted electrical discharge of current within the conductors of fastener device 24.

Figure 9A:
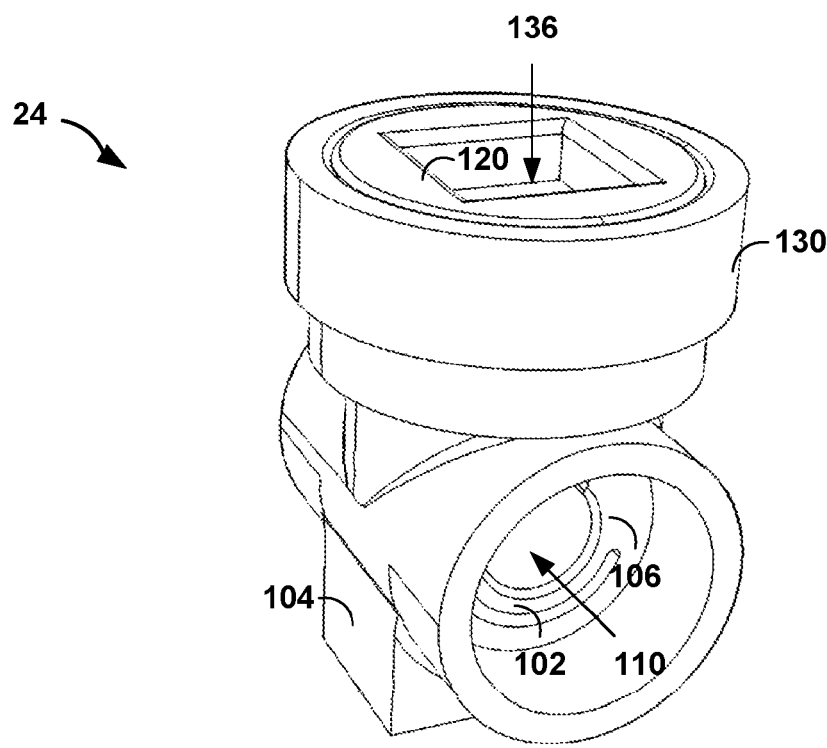
FIGS. 9A-9C are conceptual diagrams of a fastener device configured to electrically and mechanically connect a medical lead to an IMD.
Figure 9B:
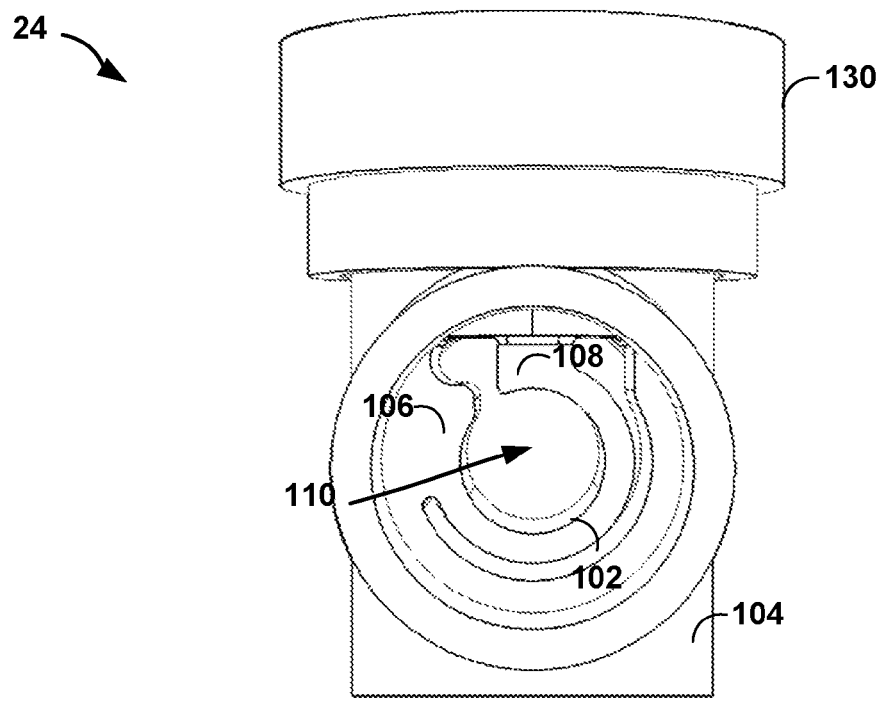
Figure 9C:
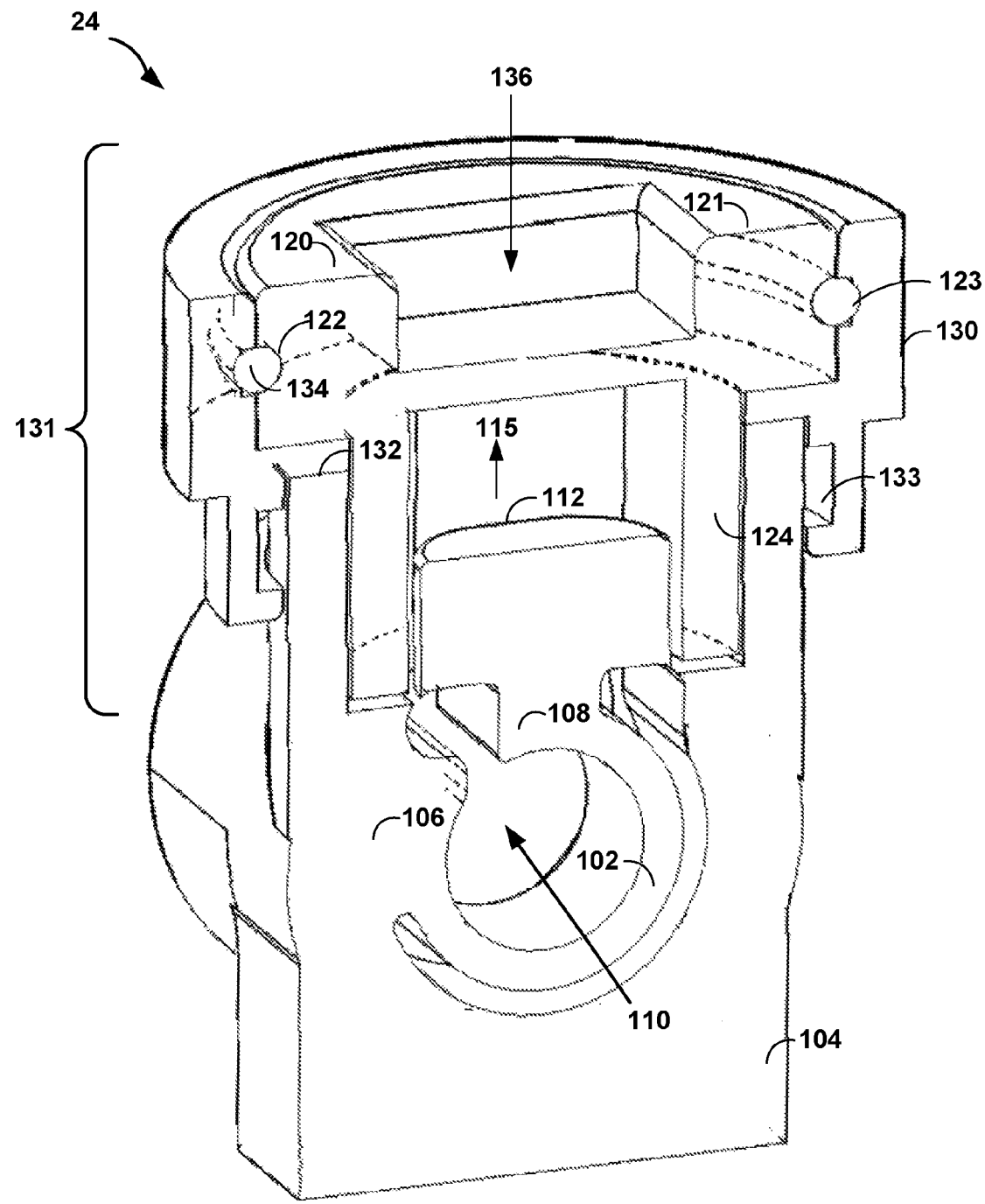

Outer fixed member 130 provides a substantially cylindrical shape and combines with the surface of cam member 124 and the surface of top portion 132 of rigid body 104 as described in FIGS. 9A-9C to operatively connect rotatable actuation member 120, outer fixed member 130, top portion 132 of rigid body 104 to form fastener device 24. Outer fixed member 130 is configured to mount on top portion 132 of rigid body 104. For example, outer fixed member 130 may be mount on top portion 132 of rigid body 104 with an epoxy or weld seal. In another example, an O-ring may be positioned within groove 133 (FIG. 9C) of outer fixed member 130 to form a fluid isolation seal between outer fixed member 130 and rigid body 104. In a further example, outer fixed member 130 may be combined with a unitary component with clamp block 101 or only rigid body 104. In some examples, outer fixed member 130 may screw onto the threads of top portion 132 of rigid body 104. In other examples, outer fixed member 130 may slide onto top portion 132 of rigid body 104. Outer fixed member 130 may be a conductive or non-conductive material. In one example, outer fixed member 130 is titanium. In another example, outer fixed member 130 is polymer such as PEEK or other suitable material.

As shown in FIG. 6, clamp block 101 includes clamp 102 and rigid body 104. Clamp 102 defines the perimeter of clamp aperture 110 between first end 106 of clamp 102 which is connected to a side of rigid body 104 and second end 108 of clamp 102 which is connected to clamp protrusion 112. Clamp protrusion 112 extends into rigid body aperture formed by top portion 132 of rigid body 104. Top portion 132 of rigid body 104 may be a substantially cylindrical shape. In the example of FIG. 6, top portion 132 is formed in the shape of a ring and extends above rigid body 104 forming the perimeter of the rigid body aperture, which surrounds clamp protrusion 112. Opening and closing of clamp aperture 110 is accomplished by actuation of clamp protrusion 112 using actuator 131 including rotatable actuation member 120 and outer fixed member 130.

In order to secure the proximal end of a medical lead, a clinician positions the proximal end of the medical lead within clamp aperture 110, and then actuates rotatable actuation member 120. Actuation of rotatable actuation member 120 reduces the perimeter of clamp aperture 110 as clamp protrusion 112 is moved, thereby reducing the space between first end 106 and second end 108 of clamp 102 and applying a compressive force on the perimeter of the proximal the medical lead. The compressive force applied about the perimeter of the proximal end of the medical lead may be substantially uniform due to the construction of fastener device 24. By applying a compressive force on the perimeter of the proximal end of the medical lead within clamp aperture 110 of clamp 102, the medical lead may be secured by fastener device 24, connector block 22, and ultimately IMD 20 as described in FIGS. 1-3.

Figure 7A:
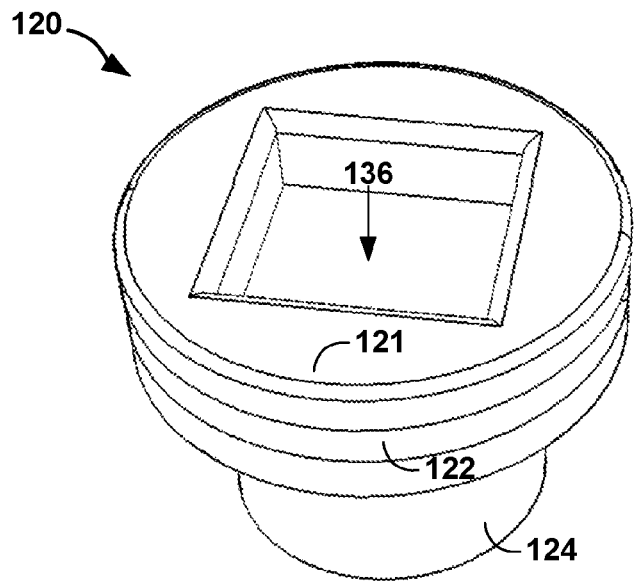
FIGS. 7A-7C are conceptual diagrams of a rotatable actuation member configured to actuate on a clamp protrusion.
Figure 7B:
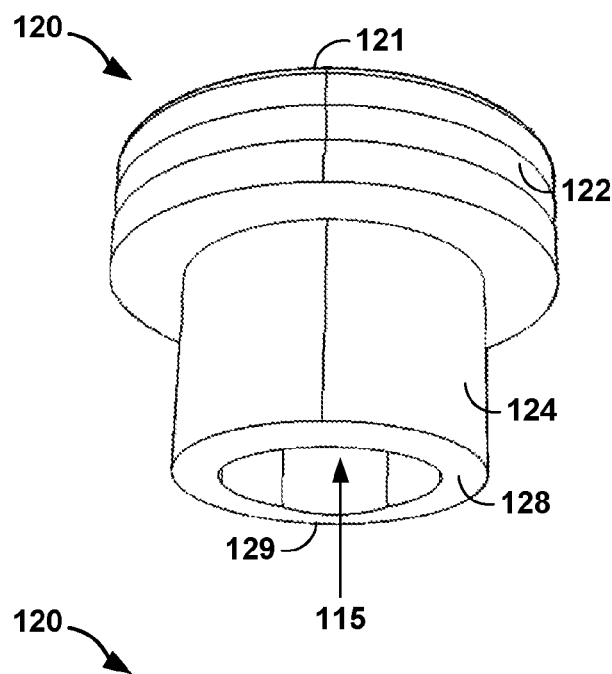
Figure 7C:
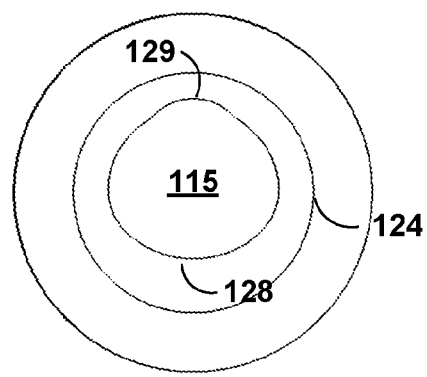

FIGS. 7A-7C illustrate rotatable actuation member 120. Rotatable actuation member 120 includes a top portion 121 and cam member 124. As best shown in FIG. 7A, top portion 121 provides a cylindrical shape with an actuation recess 136 in its top surface and a circumferential groove 122 about its perimeter. Cam member 124 is located opposite actuation recess 136. As shown in FIG. 7A, actuation recess 136 is square and configured to receive a square bit. In other examples, actuation recess 136 may be a standardized recess for use with a Phillips screwdriver, an allen wrench, torx wrench, a bristol wrench, or any other device capable of actuating rotatable actuation member 120. In other examples, rotatable actuation member 120 may include a lever to facilitate rotation. For example, such a lever may be actuateable by a clinician by hand or with a tool, such as a forceps.

As best shown in FIG. 7B, cam member 124 forms a substantially cylindrical shape with a cam recess 115 in the surface of cam member 124 that opposes top portion 121. Cam recess 115 is configured to receive protrusion 112 of clamp 102 as described in FIGS. 9A-9C or protrusions 113A, 113B of clamp 103 as described in FIG. 11.

Cam member 124 provides a generally cylindrical outer surface to facilitate rotation of rotatable actuation member 120 within rigid block aperture 114 of clamp block 101 about a central axis. As best shown in FIG. 7C, cam member 124 includes a thinner first portion 129 and a thicker second portion 128 providing an interior surface of cam member 124 that combines with the surface of protrusion 112 of clamp 102 as described in FIGS. 9A-9C or protrusions 113A, 113B of clamp 103 as described in FIG. 11 to facilitate actuation of the flexible clamp in response to the rotation of rotatable actuation member 120. In this manner, the irregular shape of cam recess 115 represents a cam when combined with protrusion 112 of clamp 102 as described in FIGS. 9A-9C or protrusions 113A, 113B of clamp 103 as described in FIG. 11. In another example of cam member 124, first portion 129 may be a notch and second portion 128 may be a uniform perimeter defining cam recess 115. In other examples, first portion 129 and second portion 128 may form a symmetrical oblong shape in the surface of cam member 124.

Figure 8A:
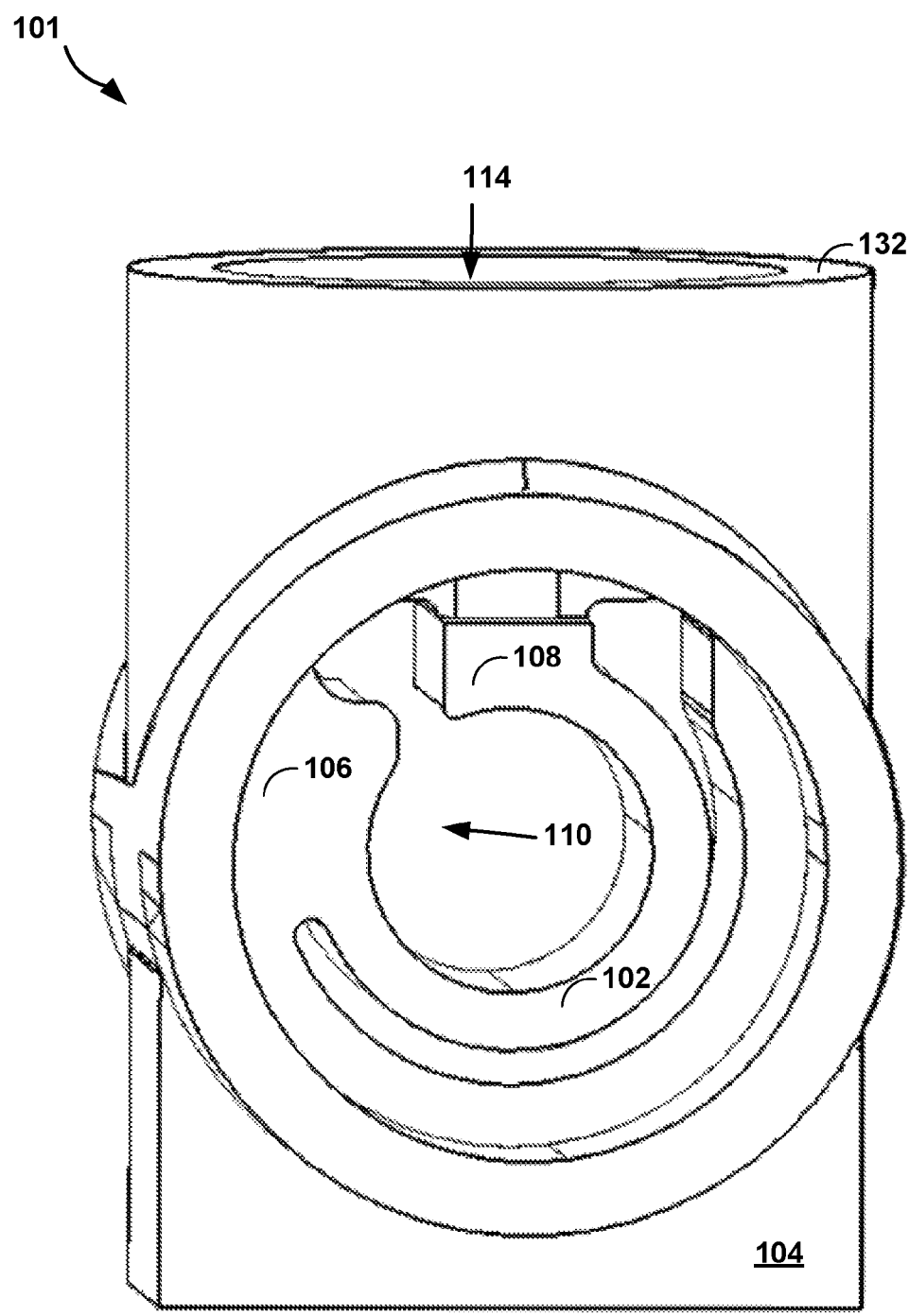
FIGS. 8A-8C are conceptual diagrams of a rigid block with an integrated flexible clamp.
Figure 8B:
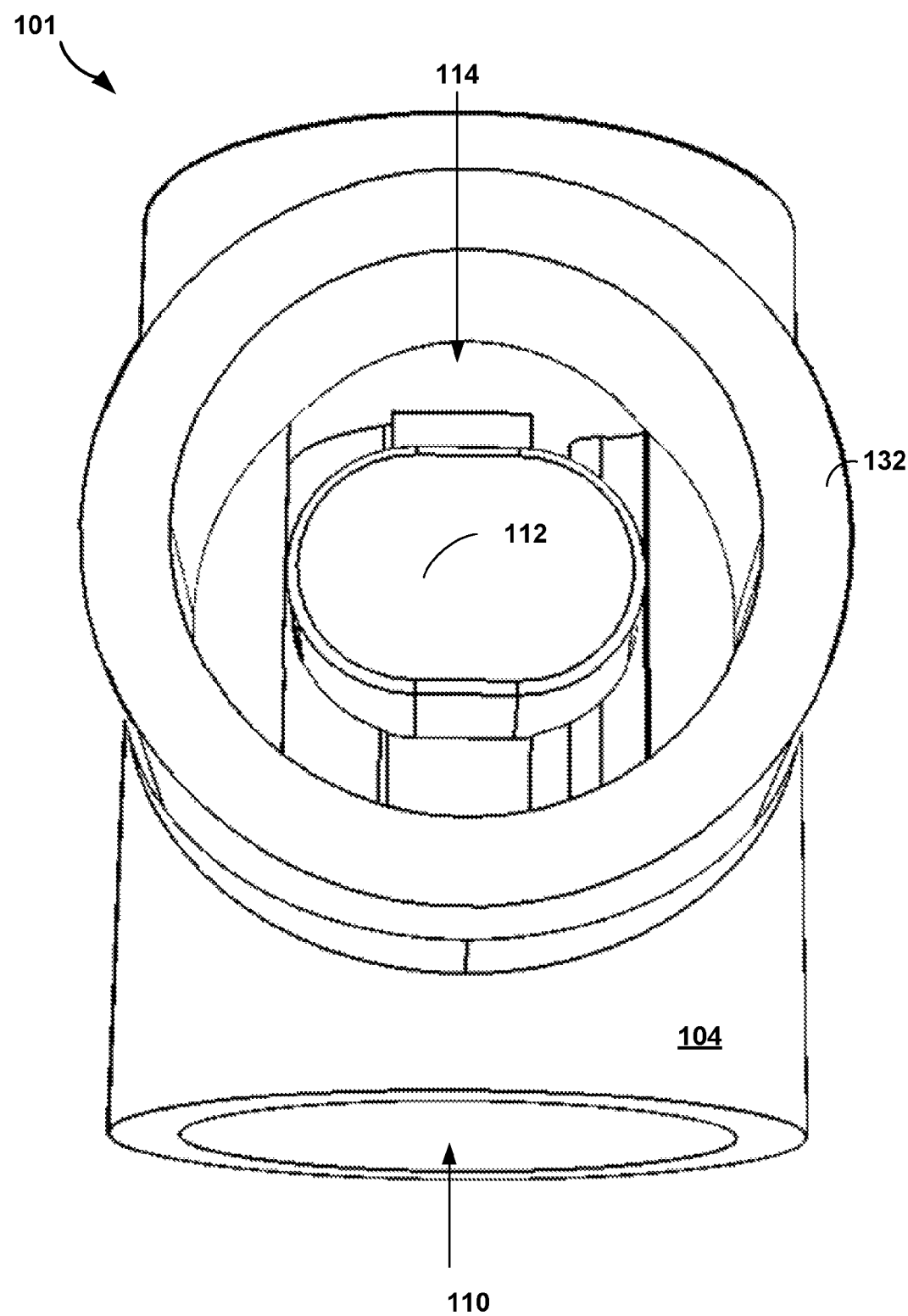
Figure 8C:
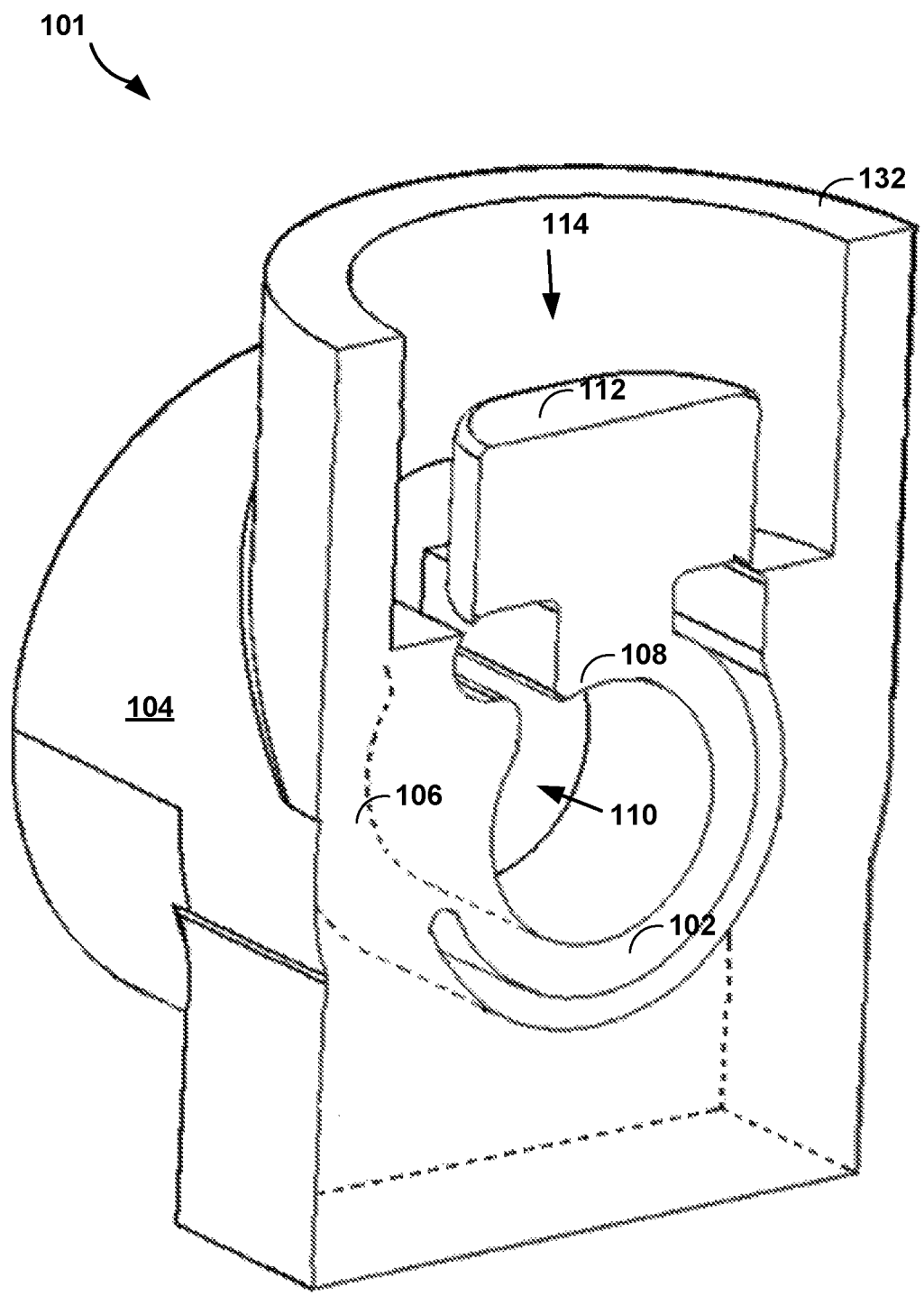

FIGS. 8A-8C illustrate examples of clamp block 101, which includes clamp 102 and rigid body 104. As best shown in FIG. 8A, clamp 102 forms the perimeter of clamp aperture 110 between first end 106 of clamp 102 which is connected to a side of rigid body 104 and second end 108 of clamp 102, which is connected to clamp protrusion 112. Opening and closing of clamp aperture 110 is accomplished by actuation of clamp protrusion 112 using rotatable actuation member 120. In other examples, a different mechanism, such as a screw or lever or any other suitable technique may be used to actuate clamp protrusion 112.

Clamp 102 is connected to and surrounded by rigid body 104, which connects to the side of rigid body 104 by first end 106 of clamp 102. Clamp 102 forms a partial ring with a cut out between first end 106 and second end 108 of clamp 102. In some examples, clamp aperture 110 is substantially circular. In other examples, clamp aperture 110 is substantially similar in shape to the perimeter of an electrical contact of a medical lead configured to be electrically and mechanically connected to fastener device 24.

As best shown in FIG. 8B, rigid body 104 includes clamp aperture 110 and top portion 132. In an example of FIG. 8B, rigid body 104 further includes clamp protrusion 112 integrated into and surrounded by rigid body 104 and extending into rigid block aperture 114 of rigid body 104 defined by top portion 132.

Clamp protrusion 112 is connected to second end of 108 of clamp 102 and may be provide an oblong shape. In the example of FIG. 8B, clamp protrusion 112 is oblong with the widest portion of clamp protrusion 112 perpendicular to the widest portion of the bore of clamp block 101. In another example, clamp protrusion 112 is oblong with the widest portion of clamp protrusion 112 parallel to the widest portion of the bore of clamp block 101. In some examples, clamp protrusion 112 may be an oblong shape extending beyond top portion 132 of rigid body aperture 114 of rigid body 104. The oblong and noncircular of shape clamp protrusion 112 combines with the noncircular shape of cam recess 115 of rotatable actuation member 120 (FIG. 7C).

Top portion 132 of rigid body 104 may be a substantially cylindrical shape. In the example of FIG. 8B, top portion 132 is formed in the shape of a ring and extends above rigid body 104 forming the perimeter of rigid body aperture 114, which surrounds clamp protrusion 112. In other examples, clamp block 101 may not include top portion 132, and rigid body aperture 114 may be defined by rigid body 104.

As best shown in FIG. 8C, clamp 102 forms a ring with a cut out between first end 106 and second end 108 of clamp 102 to define the perimeter of clamp aperture 110. In some examples, the perimeter of clamp 110 is substantially circular. In other examples, the perimeter of clamp 110 may provide a different shape. For example, the perimeter of clamp 110 may be substantially similar to the perimeter of a noncircular electrical contact at the proximal end of a medical lead. First end 106 of clamp 102 is operatively connected to the side of rigid body 104 and second end 108 is operatively connected to clamp protrusion 112. Clamp protrusion 112 forming an oblong shape with the widest portion perpendicular to the widest portion of the bore of clamp block 101 extends into rigid body aperture 114 defined by top portion 132 of rigid body 104. In some examples, top portion 132 forms a circular ring defining the perimeter of rigid body aperture 114. In other examples, top portion 132 forms a non-circular shape, defining the perimeter of rigid body aperture 114. In examples of top portion 132 forming a non-circular shape, the rotatable actuation member may be a screw as described in FIG. 10.

Clamp block 101 may be formed out of conductive material, such as titanium. In one example, clamp block 101 may be milled using standard milling processes, such as EDM. For example, clamp block 101 may be milled from a single block of material such that rigid body 104 is operatively connected to clamp 102, integrating clamp 102 into the interior of rigid body 104.

FIGS. 9A-9C illustrate fastener device 24 in a fully assembled configuration. Fastener device 24 includes clamp block 101, which includes clamp 102 and rigid body 104 and further includes outer fixed member 130, O-ring 134 and rotatable actuation member 120.

As best shown by FIG. 9C, cam recess 115, which is defined by cam member 124 of rotatable actuation member 120, is operatively connected to outer fixed member 130 to form actuator 131. In other examples, rotatable actuation member 120 may include cam member 124 positioned in rigid block aperture 114 to surround clamp protrusion 112 extended into cam recess 115. As best shown in FIG. 9C, actuator 131 facilitates sealing between an external environment and the interior of fastener device 24. In particular, actuator 131 includes O-ring 134 within groove 122 in rotatable actuation member 120 and groove 123 in outer fixed member 130. O-ring 134 provides a seal between rotatable actuation member 120, outer fixed member 130, and top portion 132 of rigid body 104. Rotatable actuation member 120 includes actuation recess 136, which may be a standardized aperture for use with a Phillips screwdriver, an allen wrench, torx wrench, a bristol wrench, or any other shape to facilitate rotation of rotatable actuation member 120 with a standard or proprietary tool. In other examples, rotatable actuation member 120 may include a lever to facilitate rotation. For example, such a lever may be actuateable by a clinician by hand or with a tool, such as a forceps.

Upon actuation of rotatable actuation member 120 by actuation recess 136, cam member 124, including the thinner first portion 129 and thicker second portion 128 forming an oblong shape, presses on clamp protrusion 112 to operably open or close clamp 102. More particularly, as the clamp protrusion 112 is actuated on by cam member 124 in cam recess 115, the perimeter of clamp aperture 110 is changed according to the position of first portion 129. In one example, the perimeter of clamp aperture 110 is reduced as first portion 129 is moved over first end 106 of clamp 102. In another example, the perimeter of clamp aperture 110 is expanded as thicker second portion 128 is moved over first end 106 of clamp 102. Generally, the change of in perimeter of clamp aperture 110 is limited by the space between first end 106 of clamp 102 and second end 108 of clamp 102. In other examples, the change of in perimeter of clamp aperture 110 overlaps first end 106 of clamp 102 with second end 108 of clamp 102.

In order to secure the proximal end of a medical lead, a clinician positions the proximal end of the medical lead within clamp aperture 110, and then actuates rotatable actuation member 120. Actuation of rotatable actuation member 120 reduces the perimeter of clamp aperture 110 as first portion 129 of cam member 124 is moved over first end 106 of clamp 102, thereby applying a compressive force on the perimeter of the proximal the medical lead. By applying a compressive force on the perimeter of the proximal end of medical lead 16, 26A, 26B within clamp aperture 110 of clamp 102, medical lead 16, 26A, 26B may be secured by fastener device 24, connector block 22, and ultimately IMD 20. The compressive force applied about the perimeter of the proximal end of the medical lead may be substantially uniform due to the construction of fastener device 24. First portion 129 may function as a detent to lock clamp 102 in place in the closed position. In other examples, a fixation device may include a positive stop located slightly beyond the maximum compressive force in order to lock clamp 102 in place in the closed position.

In order to release the proximal end of a medical lead from fastener device 24, a clinician turns rotatable actuation member 120 to disengage clamp protrusion 112 from first portion 129, which may function as a detent. Turning rotatable actuation member 120, the perimeter of clamp aperture 110 is expanded as second portion 128 of cam member 124 is moved over first end 106 of clamp 102, releasing the compressive force on the perimeter of the proximal end of the medical lead. By releasing the compressive force on the perimeter of the proximal end of the medical lead within clamp aperture 110 of clamp 102, the medical lead may be released by fastener device 24, connector block 22, and ultimately IMD 20.

In another example, clamp 102 may have one or more positive stops to prevent actuation of rotatable actuation member 120 beyond a specific rotation. For example, in FIG. 9C, first end 106 of clamp 102 forms connects to rigid body 104, but also forms a positive stop to second end 108 of clamp 102. In other examples, rotatable actuation member 120 may also have one or more positive stops to prevent actuation of rotatable actuation member 120 beyond a specific rotation. For example, cam member 124 may contain a groove substantially surrounding the surface of cam member 124, and rigid body aperture 114 of rigid body 104 may have a notch in the groove of cam member 124 that acts as a positive stop to prevent rotatable actuation member 120 from rotating beyond a specific rotation. By utilizing positive stops, fastener device 24 can be configured to provide specific compression pressures or forces on the electrical contact in clamp aperture 110. The specific compression pressures may provide better seals and/or prevent crushing or pinching of the electrical contact.

Figure 10:
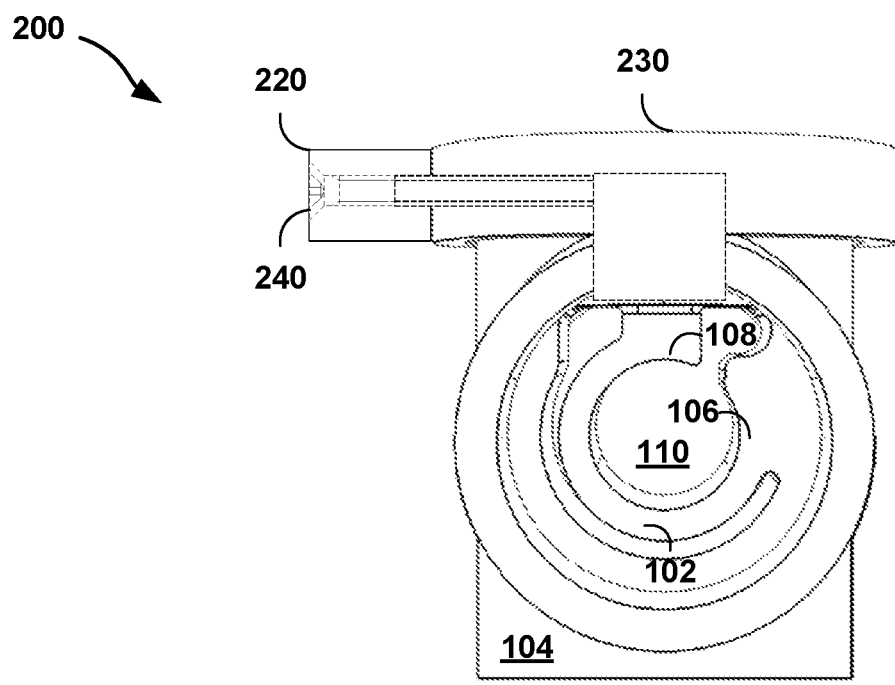
FIG. 10 is a conceptual diagram of a fastener device including a screw to act on a clamp protrusion to actuate a flexible clamp.

FIG. 10 is a conceptual diagram of fastener device 200. Fastener device 200 is substantially similar to fastener device 24 with the exception that rotatable actuation member 220 provides screw 240 instead of a cam to actuate protrusion 112 of clamp 102. In the example of fastener device 200, screw 240 may be placed on an axis extending through outer fixed member 230 and rigid body 104 to protrusion 112 of clamp 102 in a generally perpendicular orientation to the central axis of clamp aperture 110. Upon actuation of screw 240, screw 240 operates to change the perimeter of clamp aperture 110 compressing or deapplying a compressive force on the perimeter of the electrical contact within clamp aperture 110 securing or releasing the electrical contact in clamp aperture 110.

Figure 11:
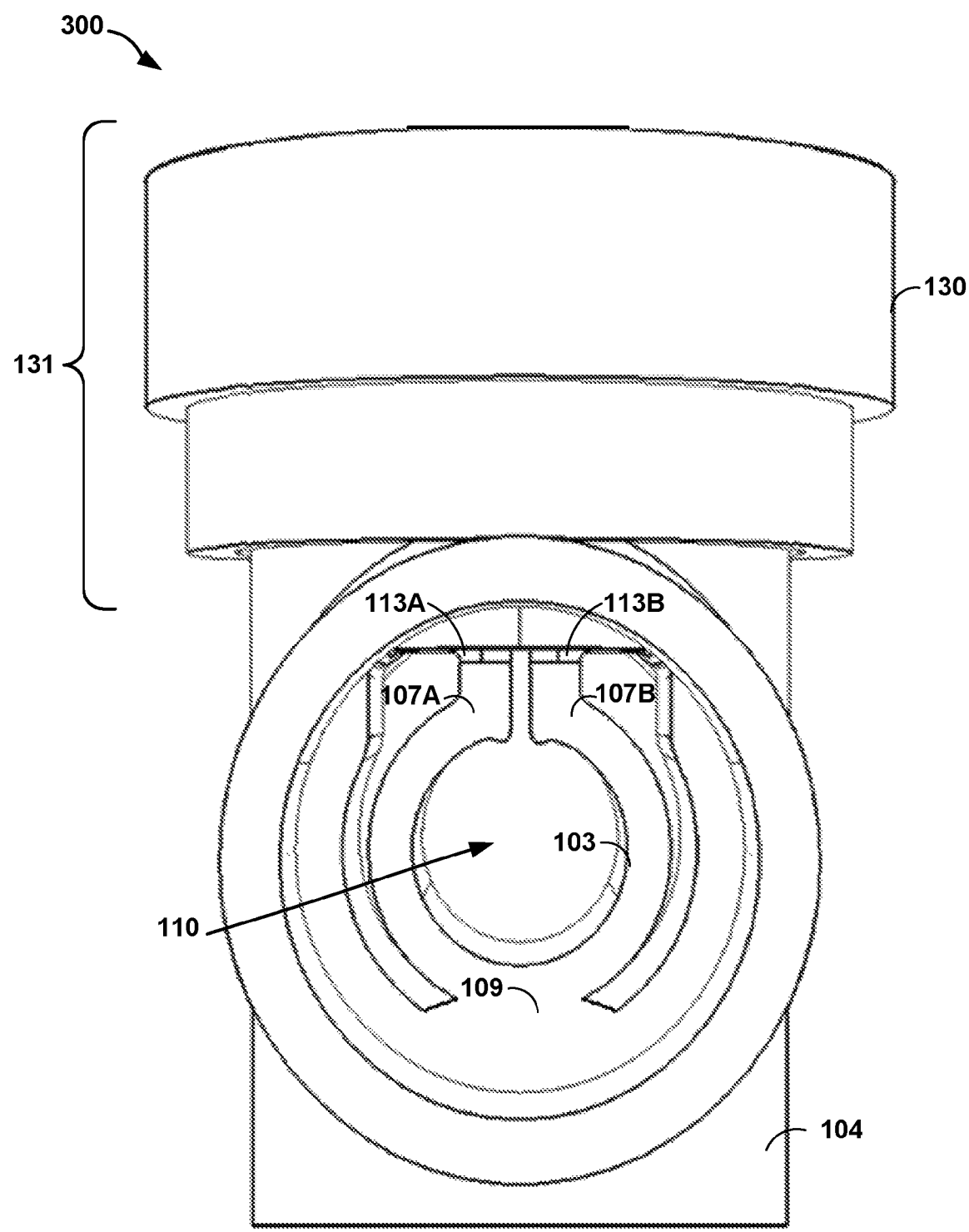
FIG. 11 is a conceptual diagram of a fastener device configured to electrically and mechanically connect a medical lead to an IMD.

FIG. 11 is a conceptual diagram illustrating an example of fastener device 300 configured to electrically and mechanically connect a medical lead to an IMD. In the example of FIG. 11, fastener device 300 includes components from fastener device 24 of FIGS. 7A-7C, 7, 8A-8C, and 9A-9C such as rigid body 104, clamp aperture 110, rigid block aperture 114, top portion 132 of rigid body 104, and actuator 131 including outer fixed member 130 and rotatable actuation member 120 with actuation recess 136, groove 122 with O-ring 134, cam member 124 including first portion 129 and second portion 128 defining cam recess 115.

In the example of FIG. 11, fastener device 300 further includes components of fastener device 24 of FIGS. 7A-7C, 7, 8A-8C, and 9A-9C such as clamp 103, first end 107A of clamp 103 operatively connected to clamp protrusion 113A, connection 109 of clamp 103 operatively connected to rigid body 104, second end 107B of clamp 103 operatively connected to clamp protrusion 113B.

In one example of fastener device 300, clamp 103, rigid body 104, first end 107A, second end 107B, and clamp protrusion 113A, 113B may be of unitary construction. In another example, clamp 103, rigid body 104, first end 107A, second end 107B, and clamp protrusion 113A, 113B may be machined using standard machining techniques, such as milling followed by wire EDM process. In other examples, clamp 103, first end 107A, second end 107B, clamp protrusion 113A, 113B, may be made of conductive material, such as titanium.

In the example of FIG. 11, clamp 103 forms a perimeter of clamp aperture 110 between first end 107A operatively connected to clamp protrusion 113A and second end 107B operatively connected to clamp protrusion 113B, which is operatively connected to rigid body 104 by connection 109 between first end 107A and second end 107B. In some examples, clamp protrusions 113A, 113B extends into cam recess 115 which is defined by cam member 124 of rotatable actuation member 120 which may be operatively connected to outer fixed member 130 to form actuator 131 which may also be operatively connected to rigid body 104. Actuator 131 may form gasket between rotatable actuation member 120 and outer fixed member 130 utilizing groove 122 and O-ring 134.

Upon actuation of rotatable actuation member 120 by actuation recess 136, cam member 124, including thinner first portion 129 and thicker second portion 128 form an oblong shape, presses on clamp protrusions 113A, 113B, which are extending into cam recess 115 to operably open or close clamp 103. More particularly, as the clamp protrusions 113A, 113B are actuated on by cam member 124 in cam recess 115, the perimeter of clamp aperture 110 is changed according to the position of first portion 129. In one example, the perimeter of clamp aperture 110 is reduced as first portion 129 is moved between first end 107A and second end 107B of rigid body 104. In another example, the perimeter of clamp aperture 110 is expanded as first portion 129 is moved over first end 107A or second end 107B. In other examples, the shape by first portion 129 and second portion 128 into the surface of cam member 124 is symmetrically oblong.

In order to secure the proximal end of a medical lead, a clinician positions the proximal end of the medical lead within clamp aperture 110, and then actuates rotatable actuation member 120 until clamp protrusion 112 engages first portion 129, which may function as a detent. Actuation of rotatable actuation member 120 reduces the perimeter of clamp aperture 110 as first portion 129 of cam member 124 is between first end 107A and second end 107B of rigid body 104, thereby applying a compressive force on the perimeter of the proximal the medical lead. By applying a compressive force on the perimeter of the proximal end of medical lead 16, 26A, 26B within clamp aperture 110 of clamp 103, medical lead 16, 26A, 26B may be secured by fastener device 300, connector block 22, and ultimately IMD 20. The compressive force applied about the perimeter of the proximal end of the medical lead may be substantially uniform due to the construction of fastener device 300.

In order to release the proximal end of a medical lead from fastener device 24, a clinician turns rotatable actuation member 120 to disengage clamp protrusion 112 from first portion 129, which may function as a detent. Turning rotatable actuation member 120 in either direction, the perimeter of clamp aperture 110 is expanded as thinner first portion 129 of cam member 124 is moved over first end 107A of rigid body 104 or second end 107B of rigid body 104, releasing the compressive force on the perimeter of the proximal end of the medical lead. By releasing the compressive force on the perimeter of the proximal end of the medical lead within clamp aperture 110 of clamp 103, the medical lead may be released by fastener device 300, connector block 22, and ultimately IMD 20.

Some IMDs, such as implantable pulse generators utilize a setscrew in combination with a setscrew block to fixate the medical lead to the IMD. Therefore, during implantation of the IMD, the user turns the setscrew in the setscrew block to pinch the medical lead between the contact surface of the setscrew and the contact surface of the setscrew block. By pinching the medical lead, the user is using the setscrew to apply a non-uniform force(s) and/or pressure(s), e.g., a point load, across the contact surface of the setscrew and the medical lead and across the contact surface of the setscrew block and the medical lead. The disclosed examples of fastener device 24 as described in FIGS. 9A-9C or fastener device 300 as described in FIG. 11 may prevent crushing of the medical lead connector ring as the load is applied by the flexible clamp in a uniform manner.

In some examples, fastener device 24 as described in FIGS. 9A-9C or fastener device 300 as described in FIG. 11 may prevent movement of the medical lead as clamp 102 compresses the perimeter of the medical lead. In other examples, fastener device 24 as described in FIGS. 9A-9C or fastener device 300 as described in FIG. 11 may prevent damage to the medical lead from exposed threads of a setscrew as the medical lead is inserted into the clamp aperture 110 because the disclosed fastener devices contain no exposed threads. Moreover, fastener device 24 as described in FIGS. 9A-9C or fastener device 300 as described in FIG. 11 may also provide concentricity with respect to the isolation seals and electrical contacts because the perimeter of clamp aperture 110 may be similar to the perimeter of the proximal end of the medical lead. Additionally, in some cases the fastener device 24 as described in FIGS. 9A-9C or fastener device 300 as described in FIG. 11 may allow for reduction in size of IMD 20, medical leads 16, 26A, 26, 26B and connector block 22.

Figure 12:
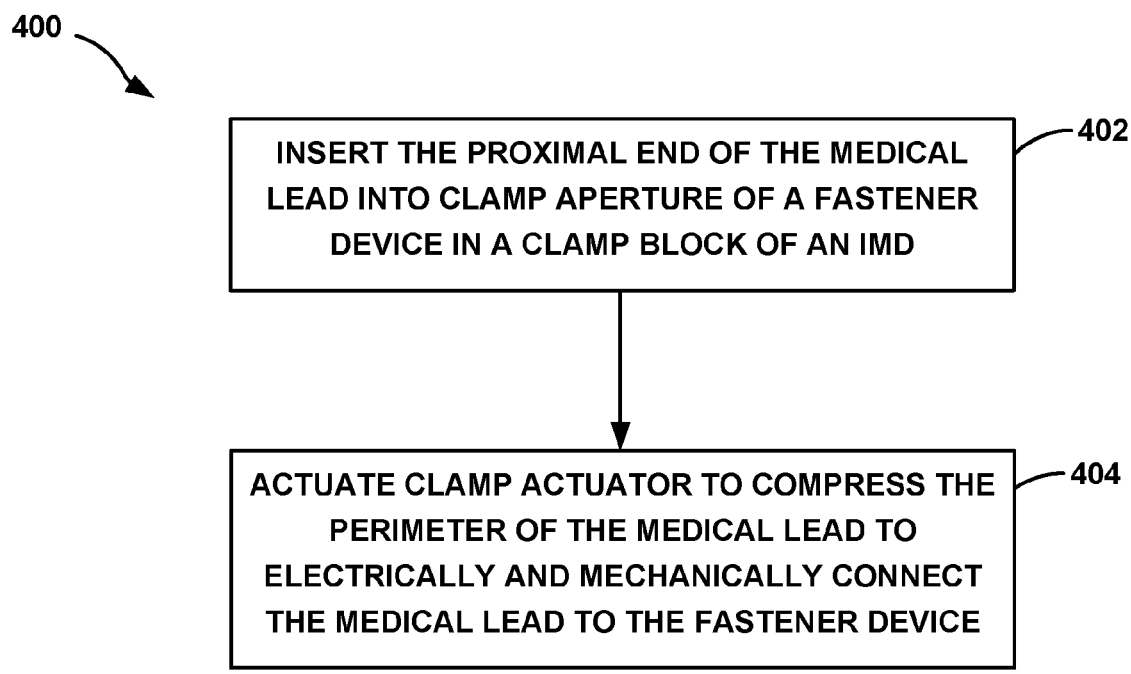
FIG. 12 is a flow diagram illustrating an example process for securing a medical lead to an IMD with a fastener device.

FIG. 12 is a flow diagram of an example process 400 for securing a medical lead 16 to an IMD 20 with fastener device 24 as described in FIGS. 9A-9C or fastener device 300 as described in FIG. 11. Process 400 includes inserting, a proximal end of the medical lead 16 including at least one electrical contact in clamp aperture 110 defined either by clamp 102 integrated into fastener device 24 or by clamp 103 integrated into fastener device 300 (402). Process 400 further includes actuating actuator 131 to actuate either clamp protrusion 112 or clamp protrusions 113A, 113B to compresses the perimeter of the electrical contact and electrically and mechanically connect the electrical contact to fastener device 24 (404).

Various examples of this disclosure have been described. These and other examples are within the scope of the following claims.

What is claimed is:

1. A fastener device for a medical device comprising:
a flexible clamp forming a clamp aperture defining a first axis,
wherein the flexible clamp includes a clamp protrusion configured to facilitate actuation of the flexible clamp;
a rigid body,
wherein the rigid body connects to and surrounds the flexible clamp; and
an actuator comprising a rotatable actuation member, wherein rotation of the rotatable actuation member about a second axis perpendicular to the first axis is configured to actuate the clamp protrusion to change a perimeter of the clamp aperture,
wherein the change of the perimeter of the clamp aperture by the rotatable actuation member is configured to apply a compressive force about a perimeter of an electrical contact of a medical lead in the clamp aperture to electrically and mechanically connect the medical lead to the fastener device.

2. The fastener device of claim 1, wherein the perimeter of the clamp aperture is substantially circular.

3. The fastener device of claim 1, wherein the flexible clamp and rigid body are formed from a unitary construction.

4. The fastener device of claim 3, wherein the flexible clamp and rigid body are formed of titanium.

5. The fastener device of claim 1, wherein the actuator includes at least one of a group consisting of:
a screw; and
a cam.

6. The fastener device of claim 5, wherein the cam comprises a non-conductive material.

7. The fastener device of claim 1, wherein the actuator further comprises an outer fixed member on the rigid body, wherein the outer fixed member defines a second aperture,
   wherein the rotatable actuation member comprises a cam member at least partially located in the second aperture, the cam member defining a cam recess configured to actuate the clamp protrusion when the rotatable actuation member is rotated,
   wherein, with the cam member at least partially located in the second aperture, at least a portion of the clamp protrusion extends within the cam recess,
   wherein the rotation of the cam member at least partially located in the second aperture of the outer fixed member causes the cam member to move relative to the rigid body and the clamp protrusion,
   wherein the movement of the cam member causes the cam recess to act on the clamp protrusion to change a distance between the rigid body and the clamp protrusion, and
   wherein the change in the distance between the rigid body and the clamp protrusion changes the perimeter of the clamp aperture.

8. The fastener device of claim 1, wherein the flexible clamp is attached to a side of the rigid body at a first end of the flexible clamp and the clamp protrusion is connected to a second end of the flexible clamp.

9. The fastener device of claim 8, wherein the change of the perimeter of the clamp aperture causes the flexible clamp to overlap the first end with the second end.

10. The fastener device of claim 1, wherein the flexible clamp is attached to the rigid body between a first end of the flexible clamp and a second end of the flexible clamp, and wherein at least one of the first end of the flexible clamp or the second end of the flexible clamp is connected to the clamp protrusion.

11. A method comprising:
   inserting a proximal end of a medical lead including at least one electrode into a clamp aperture defined by a flexible clamp of a fastener device including a flexible clamp block of an implantable medical device,
   wherein the fastener device includes:
      the flexible clamp forming the clamp aperture defining a first axis,
      wherein the flexible clamp includes a clamp protrusion configured to facilitate actuation of the flexible clamp,
      a rigid body, wherein the rigid body connects to and surrounds the flexible clamp, and
      an actuator comprising a rotatable actuation member, wherein rotation of the rotatable actuation member about a second axis perpendicular to the first axis is configured to actuate on the clamp protrusion to change a perimeter of the clamp aperture,
   wherein the change in the perimeter of the clamp aperture by the rotatable actuation member is configured to apply a compressive force about a perimeter of an electrical contact of a medical lead in the clamp aperture to electrically and mechanically connect the medical lead to the fastener device; and
   actuating the actuator configured to actuate the clamp protrusion to apply a compressive force about the perimeter of the electrical contact to electrically and mechanically connect the medical lead to the fastener device.

12. The method of claim 11, wherein the perimeter of the clamp aperture is substantially circular.

13. The method of claim 11, wherein the flexible clamp and rigid body are formed from a unitary construction.

14. The method of claim 11, wherein the actuator includes a cam.

15. The method of claim 11, further comprising implanting a medical device with the fastener device inside a patient.

16. The method of claim 11, wherein the actuator further comprises an outer fixed member on the rigid body, wherein the outer fixed member defines a second aperture,
   wherein the rotatable actuation member comprises a cam member at least partially located in the second aperture, the cam member defining a cam recess configured to actuate the clamp protrusion when the rotatable actuation member is rotated,
   wherein, with the cam member at least partially located in the second aperture, at least a portion of the clamp protrusion extends within the cam recess,
   wherein the rotation of the cam member at least partially located in the second aperture of the outer fixed member causes the cam member to move relative to the rigid body and the clamp protrusion,
   wherein the movement of the cam member causes the cam recess to act on the clamp protrusion to change a distance between the rigid body and the clamp protrusion, and
   wherein the change in the distance between the rigid body and the clamp protrusion changes the perimeter of the clamp aperture.

17. An implantable medical device comprising:
   a processor;
   a power supply;
   a stimulation generator;
   a housing forming a substantially sealed enclosure, the processor, the power supply, and the stimulation generator being located within the substantially sealed enclosure; and
   a connector block configured to provide an electrical connection between the stimulation generator and a medical lead, the connector block including at least one fastener device comprising:
      a flexible clamp forming a clamp aperture defining a first axis,
      wherein the flexible clamp includes a clamp protrusion configured to facilitate actuation of the flexible clamp;
      a rigid body,
      wherein the rigid body connects to and surrounds the flexible clamp; and
      an actuator comprising a rotatable actuation member, wherein rotation of the rotatable actuation member about a second axis perpendicular to the first axis is configured to actuate on the clamp protrusion to change a perimeter of the clamp aperture,
      wherein the change of the perimeter of the clamp aperture by the rotatable actuation member is configured to apply a compressive force about a perimeter of an electrical contact of the medical lead in the clamp aperture to electrically and mechanically connect the medical lead to the fastener device.

18. The implantable medical device of claim 17, wherein the actuator further comprises an outer fixed member on the rigid body, wherein the outer fixed member defines a second aperture, wherein the rotatable actuation member comprises a cam member at least partially located in the second aperture, the cam member defining a cam recess configured to actuate the clamp protrusion when the rotatable actuation member is rotated, wherein, with the cam member at least partially located in the second aperture, at least a portion of the clamp protrusion extends within the cam recess, wherein the rotation of the cam member at least partially located in the second aperture of the outer fixed member causes the cam member to move relative to the rigid body and the clamp protrusion, wherein the movement of the cam member causes the cam recess to act on the clamp protrusion to change a distance between the rigid body and the clamp protrusion, and wherein the change in the distance between the rigid body and the clamp protrusion changes the perimeter of the clamp aperture.

19. The implantable medical device of claim 17, wherein the actuator further comprises a gasket including an O-ring positioned between the outer fixed member on the rigid body and the rotatable actuation member to provide a seal.

20. The implantable medical device of claim 17, further comprising the medical lead, wherein the medical lead is electrically and mechanically connected to the fastener device in that the perimeter of the electrical contact is compressed by the flexible clamp within the clamp aperture.

\* \* \* \* \*